(12) United States Patent
Herrington et al.

(10) Patent No.: US 7,740,749 B2
(45) Date of Patent: *Jun. 22, 2010

(54) GAS DRIVE ELECTROLYTIC CELL

(75) Inventors: Rodney E. Herrington, Albuquerque, NM (US); Greg C. Mich, Albuquerque, NM (US); Kevin Schwarz, Albuquerque, NM (US)

(73) Assignee: MIOX Corporation, Albuquerque, NM (US)

( * ) Notice: Subject to any disclaimer, the term of this patent is extended or adjusted under 35 U.S.C. 154(b) by 1120 days.

This patent is subject to a terminal disclaimer.

(21) Appl. No.: 11/353,317

(22) Filed: Feb. 13, 2006

(65) Prior Publication Data

US 2006/0157342 A1  Jul. 20, 2006

Related U.S. Application Data

(63) Continuation of application No. 10/785,892, filed on Feb. 23, 2004, now Pat. No. 7,005,075, and a continuation-in-part of application No. 09/907,092, filed on Jul. 16, 2001, now Pat. No. 6,736,966.

(60) Provisional application No. 60/448,994, filed on Feb. 21, 2003.

(51) Int. Cl.
  *C02F 1/46* (2006.01)
(52) U.S. Cl. .................. 205/701; 205/742; 205/746; 204/266; 204/278
(58) Field of Classification Search ............. 205/701, 205/742, 746; 204/266, 278
See application file for complete search history.

(56) References Cited

U.S. PATENT DOCUMENTS

| | | | |
|---|---|---|---|
| 1,029,580 A | 6/1912 | Bane | |
| 1,200,165 A | 10/1916 | Burgess | |
| 2,473,986 A | 6/1949 | Booth | |
| 3,222,269 A | 12/1965 | Stanton | |
| 3,234,110 A | 2/1966 | Beer | |
| 3,365,061 A | 1/1968 | Bray | |
| 3,505,215 A | 4/1970 | Bray | |
| 3,622,479 A | 11/1971 | Schneider | |

(Continued)

FOREIGN PATENT DOCUMENTS

JP   H06-246273   9/1994

(Continued)

OTHER PUBLICATIONS

Sobsey, Mark D., "Inactivation of *Cryptosporidium parvum* Oocysts and other Waterborne Microbes by Oxidants Generated Electrochemically from Sodium Chloride from Portabel Pen and Bench Scale Systems", *American Waters Works. Association Water Quality Technology Conference*, (Nov. 6, 2000).

(Continued)

*Primary Examiner*—Arun S Phasge
(74) *Attorney, Agent, or Firm*—Peacock Myers, P.C.; Philip D. Askenazy

(57) ABSTRACT

The present invention is directed to an electrolytic cell that is completely sealed during the electrolysis operation during production of oxidant. Gasses generated within the electrolysis operation, primarily hydrogen that is liberated at the cathode surface, increase the pressure within the cell, and the gas pressure is ultimately utilized to expel the oxidant from the cell chamber.

24 Claims, 4 Drawing Sheets

U.S. PATENT DOCUMENTS

| | | |
|---|---|---|
| 3,654,148 A | 4/1972 | Bradley |
| 3,749,524 A | 7/1973 | Jordan |
| 3,791,768 A | 2/1974 | Wanner |
| 3,825,122 A | 7/1974 | Taylor |
| 4,000,065 A | 12/1976 | Ladha et al. |
| 4,070,280 A | 1/1978 | Bray |
| 4,077,883 A | 3/1978 | Bray |
| 4,124,488 A | 11/1978 | Wilson |
| 4,138,210 A | 2/1979 | Avedissian |
| 4,151,092 A | 4/1979 | Grimm et al. |
| 4,187,173 A | 2/1980 | Keefer |
| 4,288,326 A | 9/1981 | Keefer |
| 4,290,873 A | 9/1981 | Weaver |
| 4,306,952 A | 12/1981 | Jansen |
| 4,321,137 A | 3/1982 | Kohler |
| 4,367,140 A | 1/1983 | Wilson |
| 4,389,311 A | 6/1983 | La Freniere |
| 4,432,876 A | 2/1984 | Keefer |
| 4,434,056 A | 2/1984 | Keefer |
| 4,496,443 A | 1/1985 | Mack et al. |
| 4,534,713 A | 8/1985 | Wanner |
| 4,560,455 A | 12/1985 | Porta et al. |
| RE32,077 E | 2/1986 | deNora et al. |
| RE32,144 E | 5/1986 | Keefer |
| 4,632,754 A | 12/1986 | Wood |
| 4,722,263 A | 2/1988 | Valentin |
| 4,724,079 A | 2/1988 | Sale et al. |
| 4,744,877 A | 5/1988 | Maddock |
| 4,756,830 A | 7/1988 | Fredkin |
| 4,759,844 A | 7/1988 | Lipschultz et al. |
| 4,761,208 A | 8/1988 | Gram et al. |
| 4,786,380 A | 11/1988 | van Duin et al. |
| 4,790,923 A | 12/1988 | Stillman |
| 4,790,946 A | 12/1988 | Jansen |
| 4,836,924 A | 6/1989 | Solomon |
| RE33,135 E | 12/1989 | Wanner, Sr., et al. |
| 4,973,408 A | 11/1990 | Keefer |
| 4,976,842 A | 12/1990 | Fowler |
| 5,085,753 A | 2/1992 | Sherman |
| 5,207,916 A | 5/1993 | Goheen et al. |
| 5,221,451 A | 6/1993 | Seneff et al. |
| 5,244,579 A | 9/1993 | Horner et al. |
| 5,306,428 A | 4/1994 | Tonner |
| 5,320,718 A | 6/1994 | Molter et al. |
| 5,354,264 A | 10/1994 | Bae et al. |
| 5,358,635 A | 10/1994 | Frank et al. |
| 5,385,711 A | 1/1995 | Baker et al. |
| 5,480,386 A | 1/1996 | Brohy |
| 5,492,534 A | 2/1996 | Athayde et al. |
| 5,496,466 A | 3/1996 | Gray |
| 5,503,736 A | 4/1996 | Schoenmeyr |
| 5,531,887 A | 7/1996 | Miers |
| 5,534,145 A | 7/1996 | Platter et al. |
| 5,540,848 A | 7/1996 | Engelhard |
| 5,558,762 A | 9/1996 | Fife et al. |
| 5,581,189 A | 12/1996 | Brenn |
| 5,597,482 A | 1/1997 | Melyon |
| 5,685,980 A | 11/1997 | Patapoff et al. |
| 5,725,758 A | 3/1998 | Chace et al. |
| 5,795,459 A | 8/1998 | Sweeney |
| 5,858,201 A | 1/1999 | Otsuka et al. |
| 5,900,212 A | 5/1999 | Maiden et al. |
| 5,911,870 A | 6/1999 | Hough |
| 5,928,490 A | 7/1999 | Sweeney |
| 5,958,229 A | 9/1999 | Filiopoulos et al. |
| 5,989,396 A | 11/1999 | Prasnikar et al. |
| 6,007,686 A | 12/1999 | Welch et al. |
| 6,110,424 A | 8/2000 | Maiden et al. |
| 6,180,014 B1 | 1/2001 | Salama |
| 6,309,523 B1 | 10/2001 | Prasnikar et al. |
| 6,524,475 B1 | 2/2003 | Herrington et al. |
| 6,632,336 B2 | 10/2003 | Kasuya |
| 6,632,347 B1 | 10/2003 | Buckley et al. |
| 6,736,966 B2 * | 5/2004 | Herrington et al. .......... 210/192 |
| 7,005,075 B2 * | 2/2006 | Herrington et al. .......... 210/748 |
| 2003/0070961 A1 | 4/2003 | Miyakawa et al. |

FOREIGN PATENT DOCUMENTS

| | | |
|---|---|---|
| JP | 2000-093961 | 4/2000 |
| JP | 2002-52074 | 2/2002 |

OTHER PUBLICATIONS

Venczel, Michael A., "Inactivation of *Cryptosporidium parvum* Oocysts and Clostridium perfringens Spores by a Mixed-Oxidant Disinfectant and by Free Chlorine", *Applied and Environmental Microbiology*, (Apr. 1997),1598-1601.

* cited by examiner

GAS DRIVE ELECTROLYTIC CELL

CROSS-REFERENCE TO RELATED APPLICATIONS

This application is a continuation application of U.S. patent application Ser. No. 10/785,892, entitled "Gas Drive Electrolytic Cell", filed on Feb. 23, 2004, which application is a continuation-in-part of U.S. patent application Ser. No. 09/907,092, entitled "Portable Water Disinfection System," filed on Jul. 16, 2001, now issued as U.S. Pat. No. 6,736,966, and which claims priority to U.S. Patent Application Ser. No. 60/448,994 entitled "Electrolytic Cell for Surface and Point of Use Disinfection", filed Feb. 21, 2003. This application is also related to U.S. patent application Ser. No. 10/785,610, entitled "Electrolytic Cell for Surface and Point of Use Disinfection", filed Feb. 23, 2004. The specifications and claims of all applications listed are incorporated herein by reference.

FIELD OF THE INVENTION

The present invention relates to an electrolytic cell producing oxidants that operates in batch mode and utilizes gas pressure generated within the cell to transfer the contents from the electrolytic cell.

BACKGROUND OF THE INVENTION

Electrolytic technology utilizing dimensionally stable anodes (DSA) has been used for years for the production of chlorine and other mixed-oxidant solutions. Dimensionally stable anodes are described in U.S. Pat. No. 3,234,110 to Beer, entitled "Electrode and Method of Making Same," whereby a noble metal coating is applied over a titanium substrate.

An example of an electrolytic cell with membranes is described in U.S. Pat. No. RE 32,077 to deNora, et al., entitled "Electrode Cell with Membrane and Method for Making Same," whereby a circular dimensionally stable anode is utilized with a membrane wrapped around the anode, and a cathode concentrically located around the anode/membrane assembly.

An electrolytic cell with dimensionally stable anodes without membranes is described in U.S. Pat. No. 4,761,208 to Gram, et al., entitled "Electrolytic Method and Cell for Sterilizing Water."

Commercial electrolytic cells have been used routinely for oxidant production that utilizes a flow-through configuration that may or may not be under pressure that is adequate to create flow through the electrolytic device. Examples of cells of this configuration are described in U.S. Pat. No. 6,309,523 to Prasnikar, et al., entitled "Electrode and Electrolytic Cell Containing Same," and U.S. Pat. No. 5,385,711 to Baker, et al., entitled "Electrolytic Cell for Generating Sterilization Solutions Having Increased Ozone Content," and many other membrane-type cells.

In other configurations, the oxidant is produced in an open-type cell or drawn into the cell with a syringe or pump-type device, such as described in U.S. Pat. No. 6,524,475 to Herrington, et al., entitled "Portable Water Disinfection System."

U.S. patent application Ser. No. 09/907,092 to Herrington, et al., entitled "Portable Water Disinfection System," the specification of which is incorporated herein by reference, describes disinfection devices that utilize, in one instance, a cell chamber whereby hydrogen gas is generated during electrolysis of an electrolyte, and provides the driving force to expel oxidant from the cell chamber through restrictive check valve type devices. In this configuration, unconverted electrolyte is also expelled from the body of the cell as hydrogen gas is generated. In an alternate configuration in the same application, hydrogen gas pressure is contained in a cell chamber during electrolysis, but the pressure within the cell chamber is limited by the action of a spring loaded piston that continues to increase the volume of the cell chamber as gas volume increases. Ultimately, a valve mechanism opens, and the spring-loaded piston fills the complete volume of the cell chamber forcing the oxidant out of the cell chamber.

In the current embodiment of the present invention, the cell chamber incorporates an inactive gas chamber at the top of the cell that allows the accumulation of gas (e.g. hydrogen gas). The gas pressure is generated, and this pressure is ultimately utilized as the sole driving force to expel the oxidant from the bottom of the cell through a valve mechanism. Utilizing this mechanism, complete electrolytic conversion of the electrolyte in the cell chamber is achieved allowing optimal operational efficiency.

Other inventions that utilize gas pressure generated from electrolysis are also described in the literature. U.S. Pat. No. 4,138,210, to Avedissian, entitled "Controlling the Pressure of a Gas Generator," describes a gas torch that utilizes an electrolytic mechanism for generating and controlling pressure of hydrogen gas that is used as the feed gas for the torch. U.S. Pat. No. 5,221,451 to Seneff, et al., entitled "Automatic Chlorinating Apparatus," describes a chlorine gas generating cell that operates at the same pressure as the treated water flow stream. Water under pressure flows through the closed cell and replenishes the electrolyte level in the cell. Partitions within the electrolytic cell maintain separation of the chlorine gas that is aspirated in the water stream. Chlorine and hydrogen gas generated within the cell maintain a pressure balance between the chlorine gas phase and the pressure of the liquid water flowing through the cell so that unconverted electrolyte is not drawn into the flowing water stream. U.S. Pat. No. 5,354,264 to Bae, et al., entitled "Gas Pressure Driven Infusion System by Hydrogel Electrolysis," describes a system that generates and controls the production of oxygen and hydrogen gas in an electrolytic hydrogel process for the purpose of closely regulating the amount of liquid drugs that are delivered under gas pressure to the human body.

BRIEF SUMMARY OF THE INVENTION

The preferred embodiment of the present invention is an apparatus to produce a disinfecting solution to treat a fluid. The apparatus comprises at least one cell. The cell comprises at least two electrodes wherein at least one electrode comprises at least one cathode and at least one electrode comprises at least one anode. The apparatus comprises a control circuit for providing an electrical potential between at least one cathode and at least one anode, wherein the control circuit is in electrical contact with at least one cathode and at least one anode.

During generation of oxidants, electrolyte is located within the cell housing between the anode and cathode, and a controlled electrical charge passes through the electrolytic solution from at least one cathode and at least one anode, thereby generating at least one oxidant in the electrolyte. An energy source in electrical contact with the control circuit delivers a controlled electrical charge having a predetermined charge value.

A headspace in the electrolytic cell accumulates generated gas under pressure for the purpose of utilizing the generated gas pressure to expel the contents of the cell on completion of electrolysis.

Prior to electrolysis, electrolyte is introduced into the cell via an inlet port. The inlet port comprises an inlet port mechanism such as a valve to seal the inlet port after the electrolyte has entered the cell. The cell further comprises an outlet port and outlet port mechanism such as a valve to seal the outlet port during electrolysis. After electrolysis, the outlet port mechanism opens and allows discharge of electrolyzed oxidant through the outlet port.

In the preferred embodiment, the apparatus comprises a positive displacement pump for transfer of the electrolyte to an interior of the cell. In an alternative embodiment, the inlet port mechanism comprises a control valve to allow transfer of electrolyte to the interior of the cell. In another embodiment of the present invention, the inlet port mechanism comprises a dual control valve to allow transfer of electrolyte to the interior of the cell while simultaneously allowing gas to vent out of the cell. Prior to electrolysis during the fill operation, gas venting, depending on system design, may be required in order to allow electrolyte to flow to the interior of the cell without restriction from gas pressure buildup in the confined space within the cell.

In another embodiment of the present invention, the inlet port mechanism comprises a check valve to allow transfer of electrolyte to the interior of the cell. During electrolysis the check valve restricts flow of gas and fluids out of the cell.

The apparatus of the present invention comprises an electrolyte storage container. The electrolyte storage container may be a permanent part of the apparatus, or it may be a replaceable electrolyte storage container. To allow free flow of electrolyte solution from the electrolyte storage container, the container comprises a vent valve to release negative pressure from within the electrolyte storage container to allow free flow of electrolyte from the container. In the preferred embodiment, the electrolyte storage container comprises a quick disconnect valve on the container discharge port to allow removal of the container from the system without loss of electrolyte from the container. In an alternative embodiment, the electrolyte storage container is collapsible.

In an alternative embodiment of the present invention, the apparatus comprises a microprocessor circuit that identifies the electrolyte storage container with system. The remaining contents of the electrolyte storage container can be determined by virtue of the microprocessor by keeping track of the number of operations of the apparatus, and knowing the volume of electrolyte used during each operational cycle.

The apparatus further comprises a fluid storage container for storage of a fluid to be treated by the oxidant solution. In the preferred embodiment, the fluid storage container comprises an oxidant measuring device. In the preferred embodiment, the oxidant measuring device is a chlorine measuring device. In an alternative embodiment of the present invention, the chlorine measuring device is a solid-state semiconductor commonly referred to as a "sensor-on-a-chip". In a further embodiment of the present invention, the oxidant measuring device comprises an oxidation reduction potential (ORP) measuring device. To ensure accuracy of the ORP measuring device, the oxidant sensor may also comprise a device for measuring temperature and pH and adjusting the ORP value for variations in temperature and pH.

In an alternative embodiment of the present invention, the apparatus comprises an oxidant storage container in lieu of a fluid storage container. Alternately, the apparatus comprises a port for injection of oxidants directly into a selected source to be treated. The source to be treated my be a closed fluid body such as a water tank, open fluid body such as a swimming pool, a pipe with fluid flowing therein, a sump such as in a cooling tower, a basin, trough, and/or a plenum for spraying oxidant into a gas stream such as an air duct or other gas stream for oxidizing constituents in the gas stream.

The apparatus of the present invention further preferably comprises a microprocessor control system. The control system measures and controls power to the anode and cathode, controls activation of the inlet port feed mechanism, the outlet port mechanism, and the oxidant measuring device. Further, the apparatus comprises an electrolyte storage container microprocessor for identifying the electrolyte storage container with the system. The electrolyte storage container microprocessor maintains a record of a number of electrolytic cycles associated with the electrolyte storage container for the purpose of determining the remaining volume and remaining number of cycles available in the electrolyte storage container. By this means, the electrolyte storage container can be removed from the system and replaced by an alternate electrolyte storage container. Data recorded in the microprocessor allows the control system of the apparatus to keep track of the remaining electrolyte in each unique electrolyte storage container.

Broadly, it is a primary object of the present invention to provide a batch mode electrolytic cell that utilizes a gas chamber space above the electrodes within a confined cell. During electrolysis, gases, primarily hydrogen gas, are utilized to expel the generated oxidant from the electrolytic cell via a cell discharge valve to a fluid to be treated, or an oxidant storage container.

A primary advantage of the present invention is that a simple gas chamber space above the electrodes within an electrolytic cell is utilized to provide the driving force to expel oxidant from the electrolytic cell to a fluid to be treated. This configuration allows complete electrolysis of the electrolyte for efficient operation, and does not rely on a flow-through cell or separate pumping devices to transfer the oxidant to the fluid to be treated. Gas pressure generated in the electrolysis process is utilized to provide the force to transfer oxidant from the cell. This configuration allows for very low cost manufacturing for applications in consumer devices, or other low fluid volume systems.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DETAILED DESCRIPTION OF THE INVENTION

The present invention comprises an electrolytic cell and method for generation of oxidants that are utilized to disinfect surfaces, liquids, or airborne contaminants.

Figure 1:
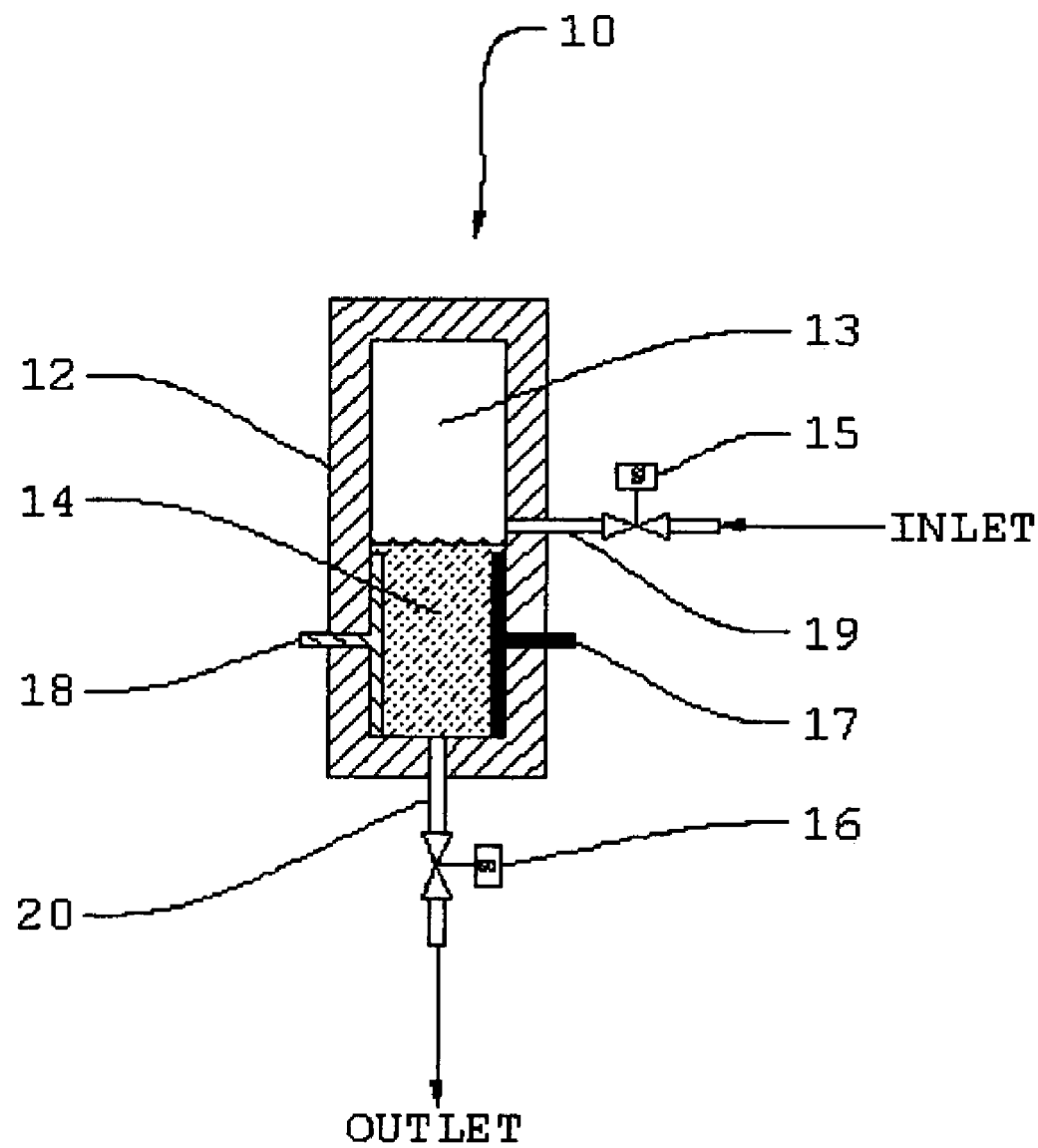
FIG. 1 is a view of an electrolytic cell with a gas chamber space above the electrodes.

Referring to FIG. 1, which shows the preferred embodiment of the invention, electrolyte solution 14, preferably, a sodium chloride brine solution is introduced into cell housing 12 which comprises positive anode 17 and negative cathode 18 wherein electrolyte solution 14 is electrolytically converted to an oxidant solution within the confined space of electrolytic cell 10. Any electrolyte solution for generating an oxidant is useful in accordance with the present invention.

During electrolysis, hydrogen gas is liberated at cathode 18 and accumulates in headspace 13. As hydrogen gas accumulates in headspace 13, gas pressure increases according to the well known gas equation, $PV=nRT$ wherein P is the pressure of the gas, V is the volume of the chamber, n is the moles of gas, R is the molar gas constant, and T is the absolute temperature. Gas pressure increases by virtue of the fact that inlet valve 15 and outlet valve 16 are both closed.

To initiate the process, outlet valve 16 is closed and inlet valve 15 is open. Electrolyte solution 14 is introduced to cell housing 12 either by gravity feed or by utilizing a fluid transfer device such as a pump to introduce the electrolyte solution 14 to interior of the cell housing 12.

After electrolyte solution 14 has been introduced into cell housing 12, inlet valve 15 is closed, and electrical power is applied across the positive electrode, anode 17, and negative electrode, cathode 18. Anode 17 and cathode 18 are sealed within cell housing 12.

During electrolysis, hydrogen gas is generated at the surface of cathode 18. The hydrogen gas bubbles rise and accumulate in headspace 13. As electrolysis continues, gas pressure within headspace 13 rises creating a pressure within cell housing 12. With proper design, approximately all of the sodium chloride within electrolyte solution 14 is efficiently converted to oxidant.

The volume of headspace 13 determines the pressure that is built up within cell housing 12. The appropriate pressure desired is a function of the system design and the required pressure needed to discharge the oxidant contents within cell housing 12 to the oxidant storage device, or preferably, the fluid to be treated. The fluid to be treated may be at zero pressure, or any other pressure such as the pressure in a normal water supply system.

Oxidant produced from the electrolysis of electrolyte solution 14 is discharged from cell housing 12 by opening outlet valve 16. Most of the hydrogen gas generated in the electrolysis process is also discharged from cell housing 12 through outlet valve 16. Efficient production of oxidant can be generated in a series of batch process sequences previously described, and can utilize the gas pressure generated in the electrolysis process to provide the force necessary to introduce the oxidant to the fluid to be treated, without the need for auxiliary pumps or transfer devices.

Figure 2:
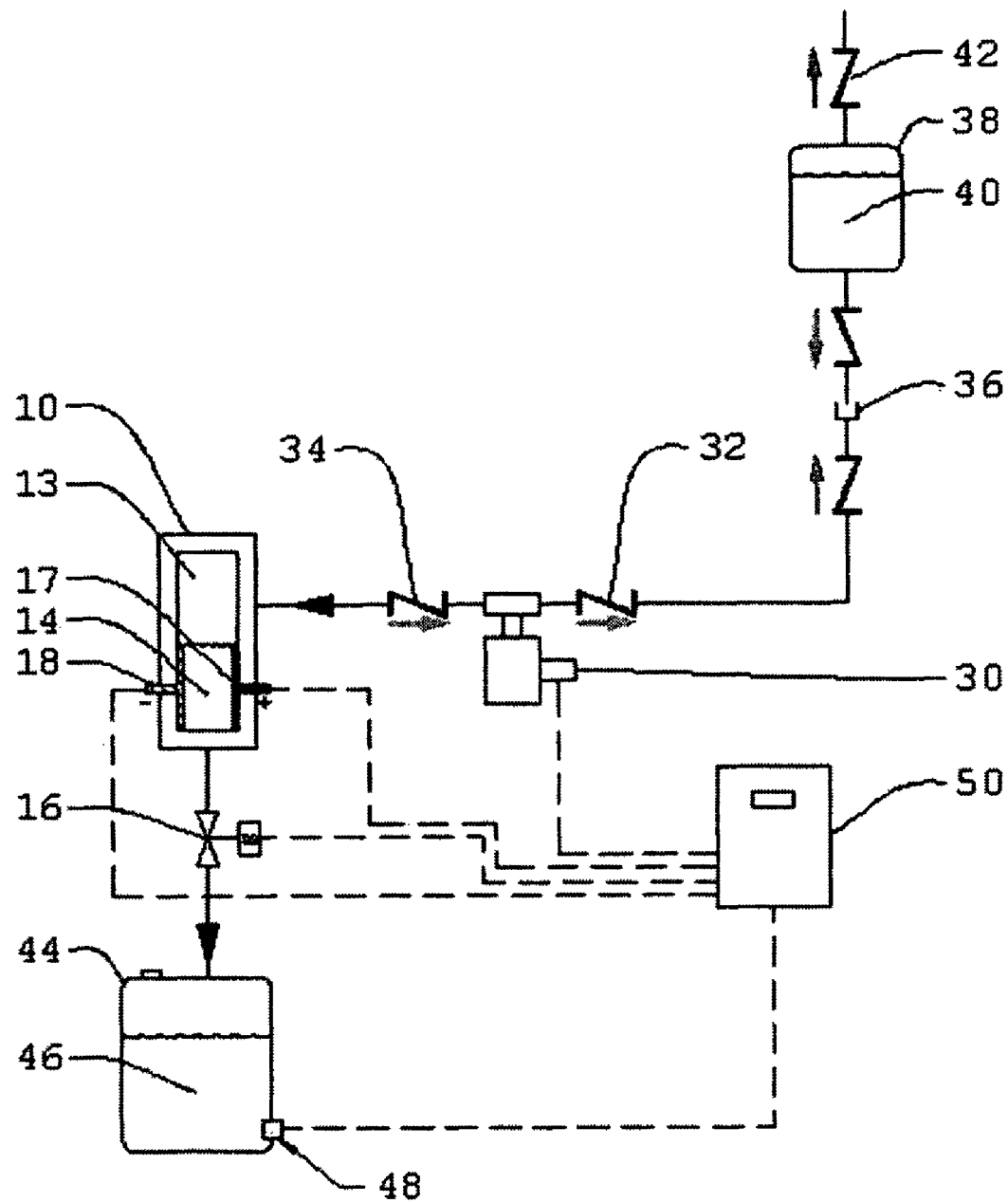
FIG. 2 is a system configuration utilizing a pump to transfer electrolyte to an electrolytic cell with a gas chamber.

The preferred embodiment of the system of the present invention is shown in FIG. 2. In the preferred embodiment, electrolytic cell 10 receives electrolyte solution 14 from an electrolyte storage container 38. Electrolysis occurs within cell 10 and the resulting oxidant solution is then transferred to fluid 46 to be treated within fluid storage device 44 which may or may not be under pressure.

In the preferred embodiment, electrolyte storage container 38 is removable for subsequent replacement by new electrolyte storage container 38. Electrolyte storage container 38 comprises vent valve 42 that allows the introduction of air into electrolyte storage container 38 as electrolyte solution 40 is drawn out of container 38 thereby avoiding negative pressure in container 38. Electrolyte storage container 38 can be quickly removed from the system by means of quick disconnect self-sealing valve 36.

In an alternative embodiment of the present invention, container 38 comprises a microchip device that identifies container 38 with the total system, and provides for electronic monitoring of the volume of the contents of container 38 based on the number of cycles of the system.

In another embodiment of the present invention, electrolyte storage container 38 can be replaced with a brine generating device. A brine generating device is filled with salt, preferably a halogen salt, and water mixes with the halogen salt to produce a liquid brine solution. The liquid brine solution performs as electrolyte 40.

In the preferred embodiment, electrolyte 40 is transferred to electrolytic cell 10 by a positive displacement pump such as diaphragm type pump 30 with inlet valve 32 and outlet valve 34 integral with the pump head. As previously described, electrolysis of the electrolyte solution occurs within cell 10 thereby converting electrolyte solution 14 to disinfecting oxidants. With proper sizing of cell 10, the concentration of electrolyte 14, and the amount and duration of electrical power applied to electrolyte 14 within cell 10, very efficient conversion of electrolyte 14 is facilitated.

Concurrent with production of oxidants, gas is generated within headspace 13 thereby developing pressure. Upon completion of electrolysis, discharge valve 16 is opened allowing the discharge of oxidant to fluid storage container 44.

In the preferred embodiment, outlet valve 16 is preferably a solenoid valve. The fluid to be treated is held in container 48. This may be a water storage tank. Alternate embodiments include a container that holds a fluid to be treated that can be used to disinfect surfaces, for instance, a spray bottle.

In the preferred embodiment, the system is controlled by microprocessor 50. In the preferred embodiment, the system is a batch process that maintains a residual oxidant value, preferable a chlorine residual value, in fluid storage container 44. Fluid storage container 44 comprises an oxidant residual monitoring device, preferably chlorine sensor 48.

In an alternative embodiment, the oxidant residual monitoring device comprises an oxidation reduction potential (ORP) sensor or chlorine sensor mounted on an integrated circuit device (aka chlorine sensor-on-a-chip).

In the preferred embodiment, the fluid level in fluid storage container 44 is not important to maintaining the desired oxidant residual value. Chlorine sensor 48 monitors the chlorine residual value via microprocessor 50. If the chlorine residual value is below the desired value, microprocessor 50 instructs the system to produce another batch of oxidant in cell 10. In this mode of operation, neither the oxidant demand of the fluid to be treated, nor the volume of fluid in the fluid storage container 44 are important to maintaining the desired chlorine residual value. If the chlorine residual value is not sufficient, microprocessor 50 continues making oxidant in batches until the desired chlorine residual is maintained.

Figure 3:
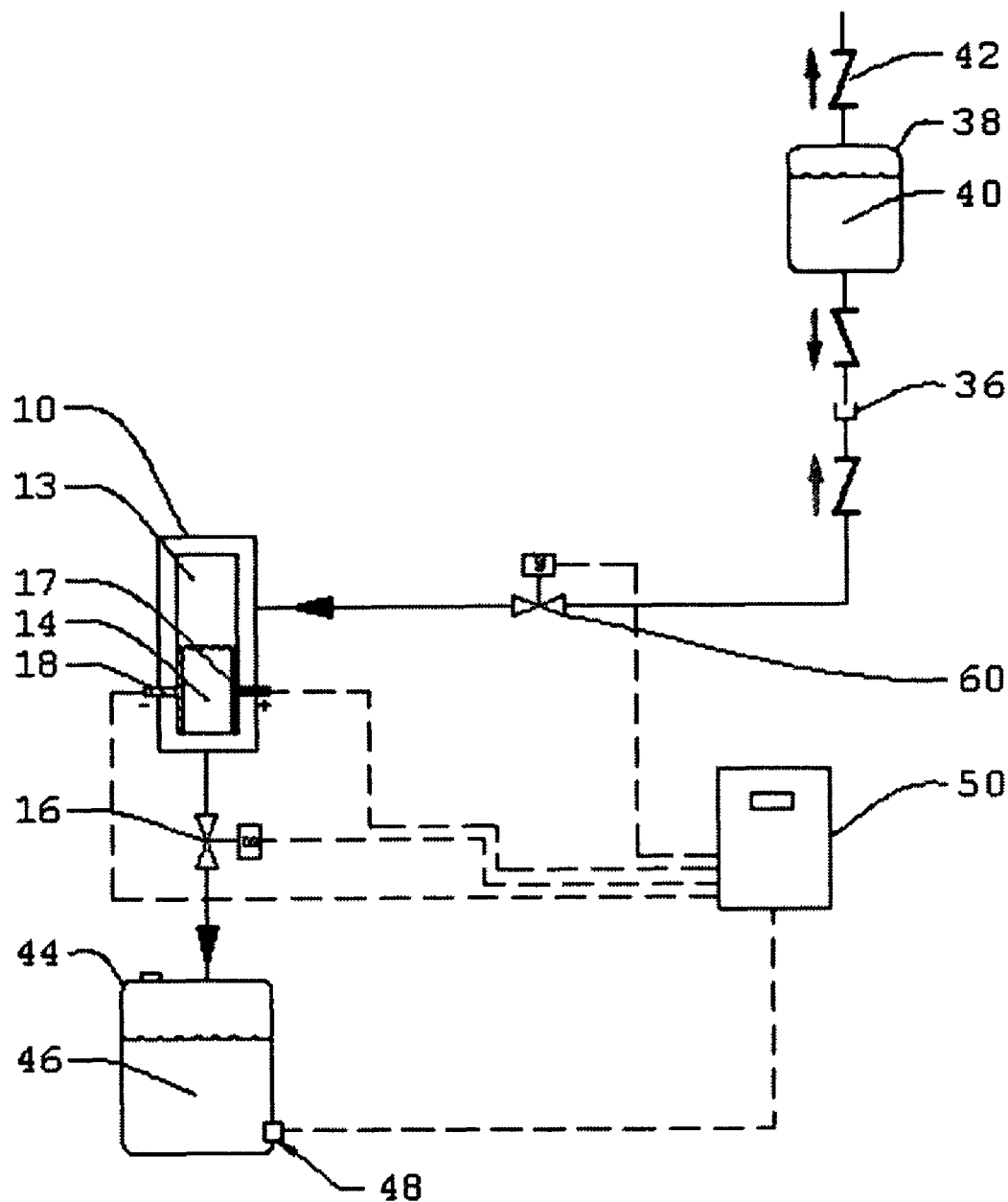
FIG. 3 is a system configuration utilizing gravity to transfer electrolyte to an electrolytic cell with a gas chamber.

In an alternative embodiment shown in FIG. 3, the electrolyte is transferred by gravity via inlet solenoid valve 60 instead of fluid transfer pump 30 shown in FIG. 2. The operational scenario with inlet solenoid valve 60 works well if fluid transfer line sizes are adequately sized to avoid flow resistance due to electrolyte fluid viscous effects or hydraulic locking that avoids transfer of vent gasses in the fluid transfer lines.

In an alternative embodiment of the present invention, inlet solenoid valve 60 is replaced with a simple check valve. With proper timing via microprocessor 50, the batch process is terminated by removing power from anode 17 and cathode 18 and opening outlet solenoid valve 16. As the contents of cell 10 are discharged, outlet solenoid valve 16 can remain open long enough for electrolyte 40 to flow into cell 10, and then outlet solenoid valve 16 is closed. Electrolyte flows through the inlet check valve and the check valve will close after electrolyte 40 has entered cell 10. The inlet check valve prevents the flow of gas from moving backwards up to electrolyte storage container 38.

Figure 4:
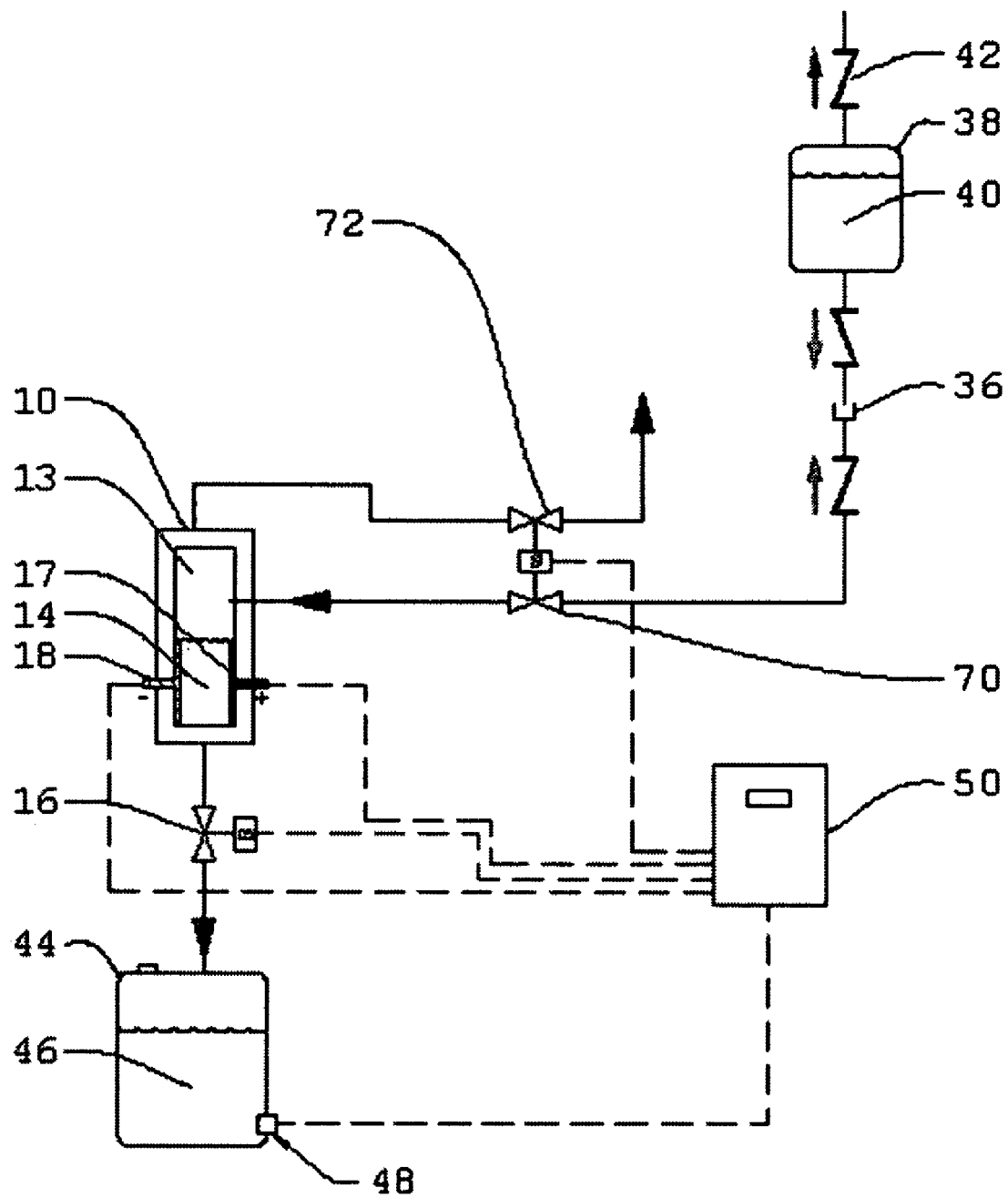
FIG. 4 is a system configuration utilizing gravity to transfer electrolyte to an electrolytic cell with a gas chamber and a dual valve mechanism to vent the cell chamber during fill.

In an alternative embodiment shown in FIG. 4, the electrolyte is transferred by gravity via dual inlet valve 70 and 72 which also incorporates a vent line to relieve pressure within electrolytic cell 10 allowing free flow of electrolyte 40 into cell 10.

Applications of the present invention are especially applicable to low-cost water treatment systems for the home-use and consumer market. However, it will be obvious to those versed in the art that this invention can be utilized in a variety of applications including spray bottle applications for surface cleaning, potable water treatment systems, wastewater treatment systems, swimming pool treatment systems, cooling tower treatment systems, and other applications where a disinfectant is utilized to treat a fluid.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An electrolytic apparatus comprising:
   an electrolytic cell comprising at least two electrodes;
   a power source in electrical contact with said at least two electrodes;
   electrolyte for placement in said cell, wherein said electrolyte does not completely fill said cell;
   a headspace within said electrolytic cell to accumulate a gas generated during electrolysis of the electrolyte;
   an outlet port for discharging electrolysis products from said cell; and
   a valve for sealing said outlet port, which valve is opened once a pressure of said gas reaches a predetermined value.

2. The apparatus of claim 1 wherein said predetermined value is sufficient to expel the electrolysis products from said cell at a desired rate.

3. The apparatus of claim 1 wherein said electrolysis products comprise at least one oxidant.

4. The apparatus of claim 1 further comprising a fluid storage container.

5. The apparatus of claim 4 wherein said electrolysis products are discharged into said container.

6. The apparatus of claim 1 further comprising a device selected from the group consisting of an oxidant measuring device, an oxidation reduction potential (ORP) measuring device, and a chlorine residual measuring device.

7. The apparatus of claim 1 further comprising a port for injection of the electrolysis products into a source to be treated, said source comprising at least one member selected from the group consisting of a closed fluid body, an open fluid body, a pipe with fluid flowing therein, a sump, a basin, a trough, and a plenum.

8. The apparatus of claim 1 further comprising an electrolyte storage container.

9. The apparatus of claim 8 wherein said electrolyte storage container is replaceable or refillable.

10. The apparatus of claim 8 wherein said electrolyte storage container further comprises a quick disconnect valve to allow flow of the electrolyte to said cell, and discontinuing flow of the electrolyte from said electrolyte storage container when said electrolyte storage container is disconnected at said quick disconnect valve.

11. The apparatus of claim 8 wherein a microprocessor circuit identifies said electrolyte storage container with said cell and measures a volume of said electrolyte storage container by virtue of a number of electrolyte-to-oxidant conversion cycles that occur within said cell.

12. The apparatus of claim 1 further comprising an oxidant storage container.

13. An electrolysis method comprising the steps of:
    providing an electrolytic cell comprising at least two electrodes;
    partially filling the cell with electrolyte;
    sealing the cell;
    providing an electrical potential between the at least two electrodes;
    generating at least one oxidant in the electrolyte;
    accumulating a gas in at least a portion of the cell which is not filled with electrolyte until a predetermined gas pressure is reached;
    expelling the at least one oxidant from the cell using the pressurized gas.

14. The method of claim 13 further comprising the step of transferring electrolyte to the cell from an electrolyte storage container.

15. The method of claim 14 further comprising the step of replacing or refilling the electrolyte storage container.

16. The method of claim 14 further comprising the steps of:
    providing a quick disconnect valve between the electrolyte storage container and the cell;
    allowing flow of the electrolyte to the cell; and
    discontinuing flow of the electrolyte from the electrolyte storage container when the electrolyte storage container is disconnected at the quick disconnect valve.

17. The method of claim 14 further comprising the step of identifying the electrolyte storage container with the cell via a microprocessor circuit and measuring a volume of the electrolyte storage container by virtue of a number of electrolyte-to-oxidant conversion cycles that occur within the cell.

18. The method of claim 13 further comprising the step of providing a fluid storage container and storing fluid within the container.

19. The method of claim 18 wherein the expelling step comprises discharging the at least one oxidant into the container.

20. The method of claim 19 further comprising the step of measuring a parameter selected from the group consisting of temperature, pH, an oxidant concentration, a chlorine residual, and an oxidation reduction potential.

21. The method of claim 20 wherein more of the at least one oxidant is added to the container if the parameter falls below a predetermined value.

22. The method of claim 13 further comprising the step of storing the at least one oxidant.

23. The method of claim 13 further comprising the step of injecting the at least one oxidant into a source to be treated, the source comprising at least one member selected from the group consisting of a closed fluid body, an open fluid body, a pipe with fluid flowing therein, a sump, a basin, a trough, and a plenum.

24. The method of claim 13 wherein the expelling step comprises opening a valve.

* * * * *